United States Patent [19]

Etheridge

[11] Patent Number: 5,108,488
[45] Date of Patent: Apr. 28, 1992

[54] SYNERGISTIC HERBICIDAL COMPOSITION

[75] Inventor: Jimmy R. Etheridge, Leland, Miss.

[73] Assignee: Valent U.S.A. Corporation, Walnut Creek, Calif.

[21] Appl. No.: 383,906

[22] Filed: Jul. 21, 1989

[51] Int. Cl.$^5$ .............................................. A01N 31/06
[52] U.S. Cl. .......................................... 71/98; 71/88; 71/96
[58] Field of Search .................................. 71/98, 96, 88

[56] References Cited

U.S. PATENT DOCUMENTS

| | | | |
|---|---|---|---|
| Re. 32,489 | 9/1987 | Luo | 71/98 |
| 4,517,013 | 5/1985 | Becker et al. | 71/98 |
| 4,640,707 | 2/1987 | Nagano et al. | 71/96 |
| 4,741,768 | 5/1988 | Frazier et al. | 71/98 |
| 4,792,605 | 12/1988 | Nagano et al. | 71/96 |

FOREIGN PATENT DOCUMENTS

85/904773  1/1985  European Pat. Off. .
WO87/01699 3/1987  PCT Int'l Appl. .

*Primary Examiner*—Richard L. Raymond
*Assistant Examiner*—B. M. Burn
*Attorney, Agent, or Firm*—Burns, Doane, Swecker & Mathis

[57] ABSTRACT

Disclosed are herbicidal compositions containing a combination of the compound 2-[1-(3-transchloroallyloxyimino)propyl]-5-(2-ethylthiopropyl)-3-hydroxy-2-cyclohexene-1-one (or a herbicidally effective salt thereof) and the compound 2-[7-fluoro-3,4-dihydro-3-oxo-4-(2-propynyl)-2H-1,4-benzoxazine-6-yl]-4,5,6,7-tetrahydro-1H-isoindole-1,3(2H)-dione. It has been found that this combination synergistically interacts so as to accelerate the post-emergent herbicidal activity of 2-[1-(3-trans-chloroallyloxyimino)propyl]-5-(2-ethylthiopropyl)-3-hydroxy-2-cyclohexen-1-one (or its salt) against grassy weeds.

18 Claims, No Drawings

SYNERGISTIC HERBICIDAL COMPOSITION

BACKGROUND OF THE INVENTION

1. Field of the Invention

The present invention is directed to a synergistic herbicidal composition having an enhanced speed-up or acceleration in its post-emergent herbicidal activity against grassy weeds. In particular, the present invention is directed to a herbicidal composition containing a herbicidally effective amount of the compound 2-[1-(3-trans-chloroallyloxyimino)propyl]-5-(2-ethylthiopropyl)-3-hydroxy-2-cyclohexen-1-one or a herbicidally effective salt thereof. This compound is a known pre-emergent and post-emergent herbicide having herbicidal activity against grassy weeds. The composition of the present invention further contains the compound 2-[7-fluoro-3,4-dihydro-3-oxo-4-(2-propynyl)-2H-1,4-benzoxazine-6-yl]-4,5,6,7-tetrahydro-1H-isoindole-1,3-(2H)-dione in an amount effective to accelerate the post-emergent herbicidal activity of 2-[1-(3-trans-chloroallyloxyimino)propyl]-5-(2-ethylthiopropyl)-3-hydroxy-2-cyclohexen-1-one or its salt. The present invention is based upon my discovery that the compound 2-[7-fluoro-3,4-dihydro-3-oxo-4-(2-propynyl)-2H-1,4-benzoxazine-6-yl]-4,5,6,7-tetrahydro-1H-isoindole-1,3(2H)-dione unexpectedly and synergistically interacts with the compound 2-[1-(3-trans-chloroallyloxyimino)propyl]-5-(2-ethylthiopropyl)-3-hydroxy-2-cyclohexen-1-one or its salt to provide for a marked acceleration in the herbicidal activity of this latter compound against grassy weeds.

2. Description of the Related Art

U.S. Pat. Nos. 4,640,707 and 4,792,605 describe the compound 2-[7-fluoro-3,4-dihydro-3-oxo-4-(2-propynyl)-2H-1,4-benzoxazine-6-yl]-4,5,6,7-tetrahydro-1H-isoindole-1,3(2H)-dione; compounds related thereto; the preparation of such compounds; and the fact that these compounds possess herbicidal activity. In practice, while the compound 2-[7-fluoro-3,4-dihydro-3-oxo-4-(2-propynyl)-2H-1,4-benzoxazine-6-yl]-4,5,6,7-tetrahydro-1H-isoindole-1,3(2H)-dione has shown excellent herbicidal activity against dicotyledonous weeds, this compound possesses poorer post-emergent herbicidal activity against grassy weeds such as johnsongrass (*sorghum halepense*), etc.

Reissue U.S. Pat. No. 32,489 as well as European Patent Application No. 85/904 773 and International Patent Application WO 87/01699 disclose compounds such as 2-[1-(3-trans-chloroallyloxyimino)propyl]-5-(2-ethylthiopropyl)-3-hydroxy-2-cyclohexen-1-one (and salts thereof, see also U.S. Pat. No. 4,741,768 for suitable salts) as well as disclose that these compounds possess pre-emergent and post-emergent herbicidal activity against grassy weeds. In practice, while the compound 2-[1-(3-trans-chloroallyloxyimino)propyl]-5-(2-ethylthiopropyl)-3-hydroxy-2-cyclohexen-1-one (and its salts) possesses excellent herbicidal activity against grassy weeds, this compound has little or no activity against dicotyledonous weeds. Additionally, the post-emergent herbicidal activity of this compound against grassy weeds manifests itself over an extended period of time. Thus, when a herbicidally effective amount of this compound is applied against grassy weeds, a suitable high level of kill of such weeds, e.g., generally greater than 90%, usually occurs about 7-21 days after application. While this delay between application and the resulting high levels of kill may in some circumstances be acceptable or even desirable, there are also circumstances where it would be desirable for the herbicidal activity of this compound to be accelerated. For example, in no-till planting of crops such as soybeans, peanuts, corn, etc., it is common practice for the seeds to be planted either shortly before or shortly after the application of a herbicidal composition designed to completely kill all of the existing weeds without the prior tilling of the soil to remove these weeds. In this circumstance, it would be desirable for a rapid burndown (kill) of all of the weeds so that the germinating crop seeds as well as the resulting seedlings do not have competition from these weeds for soil moisture and nutrients. Such a rapid burndown should preferably occur within 5 days after application of the herbicidal composition and even more preferably within 3 days. Accordingly, it is an object of this invention to provide for a herbicidal composition containing 2-[1-(3-trans-chloroallyloxyimino)propyl]-5-(2-ethylthiopropyl)-3-hydroxy-2-cyclohexen-1-one (or its salt) in which the post-emergent herbicidal activity of this compound against grassy weeds is accelerated so that this compound could be more effectively used in herbicidal compositions employed in no-till planting.

While it is common practice to attempt to design a herbicidal composition having a broad spectrum of herbicidal activity by combining two or more herbicides with limited activity, i.e., combining a herbicide having activity against grassy weeds with a herbicide having activity against dicotyledonous weeds, such compositions often do not result in the desired herbicidal activity. This result is attributed to some sort of antagonism between the herbicidal compounds.

Accordingly, it is a further object of this invention to provide for a herbicidal composition having two or more herbicidal components which results in a complete burndown of both grassy and dicotyledonous weeds with little or no antagonism between the herbicidally active components. It is still a further object of this invention to provide for a herbicidal composition which results in the rapid burndown of grassy weeds as well as dicotyledonous weeds so that this composition could be used in no-till planting.

These and other objects are achieved by the compositions of the present invention which provide for a composition containing both the compound 2-[7-fluoro-3,4-dihydro-3-oxo-4-(2-propynyl)-2H-1,4-benzoxazine-6-yl]-4,5,6,7-tetrahydro-1H-isoindole-1,3(2H)-dione and the compound 2-[1-(3-trans-chloroallyloxyimino)propyl]-5-(2-ethylthiopropyl)-3-hydroxy-2-cyclohexen-1-one (or a herbicidally effective salt thereof). In regard to this composition, none of the above cited references disclose this combination.

SUMMARY OF THE INVENTION

As noted above, the compound 2-[1-(3-trans-chloroallyloxyimino)propyl]-5-(2-ethylthiopropyl)-3-hydroxy-2-cyclohexen-1-one (and its salts) possesses herbicidal activity against grassy weeds. In this context, the present invention is directed to the discovery that when this compound is combined with 2-[7-fluoro-3,4-dihydro-3-oxo-4-(2-propynyl)-2H-1,4-benzoxazine-6-yl]-4,5,6,7-tetrahydro-1H-isoindole-1,3(2H)-dione, this combination results in the acceleration of the post-emergent herbicidal activity of this compound. Therefore, in one of its composition aspects, the present invention is directed toward a herbicidal composition comprising a biologically inert carrier; a herbicidally effective amount of the compound 2-[1-(3-trans-chloroallyloxyimino)propyl]-5-(2-ethylthiopropyl)-3-hydroxy-2-cyclohexen-1-one or a herbicidally effective salt thereof; and an effective amount of the compound 2-[7-fluoro-3,4-dihydro-3-oxo-4-(2-propynyl)-2H-1,4-benzoxazine-6-yl]-4,5,6,7-tetrahydro-1H-isoindole-1,3(2H)-dione to accelerate the post-emergent herbicidal activity of the former compound or its salt.

As also noted above, the compound 2-[7-fluoro-3,4-dihydro-3-oxo-4-(2-propynyl)-2H-1,4-benzoxazine-6-yl]-4,5,6,7-tetrahydro-1H-isoindole-1,3(2H)-dione possesses herbicidal activity, particularly against dicotyledonous weeds. Therefore, another composition aspect of this invention is directed toward a herbicidal composition comprising a biologically inert carrier; a herbicidally effective amount of the compound 2-[1-(3-trans-chloroallyloxyimino)propyl]-5-(2-ethylthiopropyl)-3-hydroxy-2-cyclohexen-1-one or a herbicidally effective salt thereof; and a herbicidally effective amount of the compound 2-[7-fluoro-3,4-dihydro-3-oxo-4-(2-propynyl)-2H-1,4-benzoxazine-6-yl]-4,5,6,7-tetrahydro-1H-isoindole-1,3(2H)-dione. This composition also provides for the accelerated post-emergent herbicidal activity of the compound 2-[1-(3-trans-chloroallyloxyimino)propyl]-5-(2-ethylthiopropyl)-3-hydroxy-2-cyclohexen-1-one and its salts resulting in a quick burndown of both grassy and dicotyledonous weeds and is particularly useful in no-till planting of crops such as soybean, corn, peanuts, etc.

The compositions of this invention result in the accelerated burndown of grasses. Therefore, in one of its method aspects, the present invention is directed toward a method for accelerating the post-emergent herbicidal activity of the compound 2-[1-(3-trans-chloroallyloxyimino)propyl]-5-(2-ethylthiopropyl)-3-hydroxy-2-cyclohexen-1-one or a herbicidally effective salt thereof which comprises employing in combination with a herbicidally effective amount of this compound an effective amount of the compound 2-[7-fluoro-3,4-dihydro-3-oxo-4-(2-propynyl)-2H-1,4-benzoxazine-6-yl]-4,5,6,7-tetrahydro-1H-isoindole-1,3(2H)-dione to accelerate the post-emergent herbicidal activity of the former compound.

Another method aspect of the present invention is directed toward a method for killing grassy weeds which comprises applying to the grassy weeds or their growth medium, a herbicidal composition comprising a biologically inert carrier; a herbicidally effective amount of the compound 2-[1-(3-trans-chloroallyloxyimino)propyl]-5-(2-ethylthiopropyl)-3-hydroxy-2-cyclohexen-1-one or a herbicidally effective salt thereof; and an effective amount of the compound 2-[7-fluoro-3,4-dihydro-3-oxo-4-(2-propynyl)-2H-1,4-benzoxazine-6-yl]-4,5,6,7-tetrahydro-1H-isoindole-1,3(2H)-dione to accelerate the post-emergent herbicidal activity of the former compound or its salt.

Still another method aspect of the present invention is directed toward a method for killing grassy and dicotyledonous weeds which comprises applying to said weeds or their growth medium a herbicidal composition comprising a biologically inert carrier; a herbicidally effective amount of the compound 2-[1-(3-trans-chloroallyloxyimino)propyl]-5-(2-ethylthiopropyl)-3-hydroxy-2-cyclohexen-1-one or a herbicidally effective salt thereof; and a herbicidally effective amount of the compound 2-[7-fluoro-3,4-dihydro-3-oxo-4-(2-propynyl)-2H-1,4-benzoxazine-6-yl]-4,5,6,7-tetrahydro-1H-isoindole-1,3(2H)-dione.

Yet still another method aspect of the present invention is directed toward a method for the no-till planting of crops which comprises applying to the area planted with seeds for said crops either before or after the planting of said seeds, a herbicidal composition comprising a biologically inert carrier; a herbicidally effective amount of the compound 2-[1-(3-trans-chloroallyloxyimino)propyl]-5-(2-ethylthiopropyl)-3-hydroxy-2-cyclohexen-1-one or a herbicidally effective salt thereof; and a herbicidally effective amount of the compound 2-[7-fluoro-3,4-dihydro-3-oxo-4-(2-propynyl)-2H-1,4-benzoxazine-6-yl]-4,5,6,7-tetrahydro-1H-isoindole-1,3(2H)-dione. This method is particularly suited for the no-till planting of soybeans, corn, peanuts, cotton, and grain sorghum, rice, etc.

DETAILED DESCRIPTION OF THE INVENTION

The present invention is directed to compositions and methods which provide for accelerated post-emergent herbicidal activity for 2-[1-(3-trans-chloroallyloxyimino)propyl]-5-(2-ethylthiopropyl)-3-hydroxy-2-cyclohexen-1-one or a herbicidally effective salt thereof. This compound possesses both pre-emergent and post-emergent herbicidal activity against grassy weeds such as johnsongrass (*sorghum halepense*), watergrass (*echinochloa cuisgalli*), etc. When so used, this compound will result in high levels of kill, e.g. >90% of the grassy weeds, usually within 7-21 days after application. On the other hand, the compositions of this invention, which also employ this compound, result in high levels of kill of grassy weeds within 5 days after application and generally within 3 days after application. This result is surprising because the compound 2-[7-fluoro-3,4-dihydro-3-oxo-4-(2-propynyl)-2H-1,4-benzoxazine-6-yl]-4,5,6,7-tetrahydro-1H-isoindole-1,3(2H)-dione, which is also employed in the composition of the present invention, does not possess superior herbicidal activity against grassy weeds.

Prior to discussing this invention in detail, the following terms will first be defined.

"2-[1-(3-trans-chloroallyloxyimino)propyl]-5-(2-ethylthiopropyl)-3-hydroxy-2-cyclohexen-1-one or a herbicidally effective salt thereof" means the compound represented by the formula:

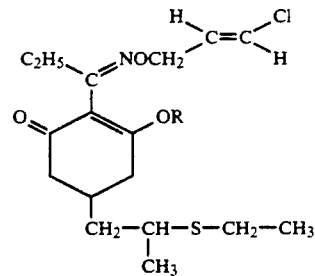

wherein R is hydrogen or a herbicidally effective salt. Representative herbicidally effective salts include $NH_4^+$, $Na^+$, $K^+$, $Ca^{++}$, etc. Methods for preparing this compound as well as its herbicidally effective salts are described in U.S. Reissue Pat. No. 32,489, U.S. Pat. No. 4,741,768, and International Patent Application No. WO 87/01699 each of which are incorporated herein in their entirety. Additional synthetic procedures are disclosed in International Patent Application No. WO 86/02065 which is also incorporated herein by reference. The nomenclature employed in U.S. Reissue Pat. No. 32,489 is different from that employed herein. Thus, the compound described herein by the nomenclature "2-[1-(3-trans-chloroallyloxyimino)propyl]-5-(2-ethylthiopropyl)-3-hydroxy-2-cyclohexen-1-one" would be described in U.S. Reissue Pat. No. 32,489 by the nomenclature "trans-2-[1-(3-chloroallyloxyimino)propyl]-5-(2-ethylthiopropyl)cyclohexane-1,3-dione". However, both names are in fact describing the same compound represented by the above formula. It is also noted that this compound exists in tautomeric forms and has optical isomers. Such tautomers and isomers are intended to be included within the above nomenclature.

"2-[7-fluoro-3,4-dihydro-3-oxo-4-(2-propynyl)-2H-1,4-benzoxazine-6-yl]-4,5,6,7-tetrahydro-1H-isoindole-1,3(2H)-dione" means the compound represented by the formula:

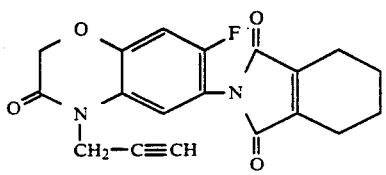

The preparation of this compound is described in U.S. Pat. Nos. 4,640,707 and 4,792,605 which are incorporated herein in their entirety.

"Herbicidally effective adjuvants" refer to compounds or compositions which while not possessing herbicidal activity, enhance the herbicidal activity of the composition. Typically, herbicidally effective adjuvants include surfactants, petroleum oils and vegetable oils and are well known in the art. Typical surfactants include nonionic surfactants, cationic surfactants, and anionic surfactants. Suitable surfactants include X-77 (registered trademark) surfactant (available from Valent USA), Triton Ag 98 (Rohm & Haas Chemical Company, Philadelphia, Pa.); LI-700 (Loveland Industries, Greely, Colo.); sodium long-chain carboxylates, alkylaryl sulfonates, sodium lauryl sulfate, polyethylene oxides, lignin sulfonates and the like. Typical vegetable oils include soybean oil, cottonseed oil, etc. Suitable herbicidally effective adjuvants include Agridex TM —available from Helena Chemical (Memphis, Tenn.); Dash TM —available from BASF; Surfel TM available from Rhone-Poulanc, Raleigh, N.C.; Red Panther Super Oil—available from Red Panther Chemical Company, Clarksdale, Miss.; Peptoil—available from Drexel Chemical Company; and the like. Without being limited by any theory, it is believed that the adjuvant enhances herbicidal activity by facilitating penetration of the herbicide(s) across the cell wall of the plant thereby allowing for more rapid uptake of the herbicide by the plant.

The adjuvant should be employed in an amount sufficient to permit enhancement of the herbicidal activity of the composition. Typically, when the herbicidal composition is a liquid, the adjuvant is employed at about 0.1 to about 2.5 percent volume/volume of the total herbicidal composition; preferably, at from about 0.25 to about 1.5 percent volume/volume; and more preferably, at from about 0.75 to about 1.25 percent volume/volume. It is understood that when an adjuvant, such as Agridex, is employed, the volume/volume percentages set forth above are for Agridex itself and not the petroleum oil portion contained therein. When the herbicidal composition is a powder or dust, the adjuvant is typically employed at about 0.1 to about 2.5 percent by weight of the total herbicidal composition.

"Accelerating the post-emergent herbicidal activity" refers to the increase in speed with which the herbicidal composition of this invention results in a kill of at least 80%, and preferably at least 90%, of the grassy weeds treated with this composition as compared to the time it takes for a similar herbicidal composition containing the compound 2-[1-(3-trans-chloroallyloxyimino)propyl]-5-(2-ethylthiopropyl)-3-hydroxy-2-cyclohexen-1-one (or its salt), as the only active herbicidal agent, to kill at least 80%, and preferably, at least 90%, of the same weeds treated with this latter composition. Preferably, the acceleration of the post-emergent herbicidal activity resulting from the composition of this invention should be at least 20%, and more preferably, at least 30%, faster than the post-emergent herbicidal activity arising from a similar herbicidal composition containing the compound 2-[1-(3-trans-chloroallyloxyimino)propyl]-5-(2-ethylthiopropyl)-3-hydroxy-2-cyclohexen-1-one as the only active herbicidal agent wherein both compositions employ the same amount of this compound. Accordingly, if the herbicidal composition containing the compound 2-[1-(3-trans-chloroallyloxyimino)propyl]-5-(2-ethylthiopropyl)-3-hydroxy-2-cyclohexen-1-one requires 10 days after application to exhibit its post-emergent herbicidal activity, the herbicidal composition of this invention should exhibit such post-emergent herbicidal activity at least by 8 days after application and preferably at least by 7 days after application. In general, accelerations in the order of 50% or more can be achieved by the composition of this invention.

COMPOSITIONS

The compositions of the present invention employ the compound 2-[1-(3-trans-chloroallyloxyimino)-propyl]-5-(2-ethylthiopropyl)-3-hydroxy-2-cyclohexen-1-one or a herbicidally effective salt thereof as a grassy weed herbicide. This compound is employed in the herbicidal composition in an amount sufficient to be herbicidally effective. That is to say sufficient amounts of this compound should be employed in the herbicidal composition so as to result in phytotoxicity to the treated grassy weeds. Generally, for both pre-emergent and post-emergent herbicidal control, this compound is employed at a rate of about 0.06 lb/acre to about 0.25 lb/acre. For post-emergence control, this compound is preferably employed in the compositions of this invention at a rate of about 0.075 lb/acre to about 0.125 lb/acre; and even more preferably at about 0.10 lb/acre.

The compositions of the present invention also employ the compound 2-[7-fluoro-3,4-dihydro-3-oxo-4-(2-propynyl)-2H-1,4-benzoxazine-6-yl]-4,5,6,7-tetrahydro-1H-isoindole-1,3(2H)-dione. The amount of this compound employed in the compositions of this invention depends on the intended use of the composition. Thus, if the composition is intended only to kill grassy weeds, then the amount of this compound used in this composition need only be sufficient to accelerate the post-emergent activity of 2-[1-(3-trans-chloroallyloxyimino)-propyl]-5-(2-ethylthiopropyl)-3-hydroxy-2-cyclohexen-1-one (or a salt thereof) against grassy weeds. In this circumstance, because the compound 2-[7-fluoro-3,4-dihydro-3-oxo-4-(2-propynyl)-2H-1,4-benzoxazine-6-yl]-4,5,6,7-tetrahydro-1H-isoindole-1,3(2H)-dione lacks superior herbicidal activity against grassy weeds, use of quantities of this compound in excess of the amount required to accelerated the post-emergent herbicidal activity of the compound 2-[1-(3-trans-chloroallyloxyimino)propyl]-5-(2-ethylthiopropyl)-3-hydroxy-2-cyclohexen-1-one (or its salt) is unnecessary. In general, amounts of about 0.5 g/acre and greater of the compound 2-[7-fluoro-3,4-dihydro-3-oxo-4-(2-propynyl)-2H-1,4-benzoxazine-6-yl]-4,5,6,7-tetrahydro-1H-isoindole-1,3(2H)-dione are sufficient to accelerate the post-emergent herbicidal activity of the compositions of this invention against grassy weeds. Preferably, the compound 2-[7-fluoro-3,4-dihydro-3-oxo-4-(2-propynyl)-2H-1,4-benzoxazine-6-yl]-4,5,6,7-tetrahydro-1H-isoindole-1,3(2H)-dione is employed at a rate of about 0.5 g/acre to 10 g/acre, and more preferably at a rate of 1 g/acre to 5 g/acre to accelerate the post-emergent herbicidal activity of the present compositions against grassy weeds.

If the composition of the present invention is intended to kill both grassy weeds and dicotyledonous weeds, then the amount of the compound 2-[7-fluoro-3,4-dihydro-3-oxo-4-(2-propynyl)-2H-1,4-benzoxazine-6-yl]-4,5,6,7-tetrahydro-1H-isoindole-1,3(2H)-dione employed in this composition should be sufficient to be herbicidally effective. That is to say sufficient amounts of this compound should be employed in the herbicidal composition so as to result in phytotoxicity to the treated dicotyledonous weeds. While amounts as low as 0.25 gm/acre of this compound are phytotoxic to some dicotyledonous weeds, this compound is generally employed in the compositions of this invention at a rate of at least about 10 g/acre in order to be phytotoxic to all of the treated dicotyledonous weeds such as is necessary when conducting no-till planting. For pre-emergent control, this compound is preferable employed at a rate of about 1 g/acre to about 75 g/acre. For post-emergent control, this compound is preferably employed in the compositions of this invention at a rate of at least about 10 g/acre; more preferably at about 20 g/acre to about 40 g/acre; and even more preferably at about 25 g/acre.

The ratio of 2-[1-(3-trans-chloroallyloxyimino)propyl]-5-(2-ethylthiopropyl)-3-hydroxy-2-cyclohexen-1-one (or its salt) to 2-[7-fluoro-3,4-dihydro-3-oxo-4-(2-propynyl)-2H-1,4-benzoxazine-6yl]-4,5,6,7-tetrahydro-1H-isoindole-1,3(2H)-dione employed in the compositions of this invention also depends on the intended use of the composition. In particular, if the composition is intended only to kill grassy weeds, then this ratio can range from about 2.5:1 to about 225:1. On the other hand, if the composition is intended for use in no-till planting, then this ratio can range from about 1:1.5 to about 10:1, with a preferred ratio of 2:1.

In a preferred embodiment, the compositions of this invention also employ a herbicidally effective adjuvant described above at rates which are also described above. Preferred adjuvants are petroleum oil based or vegetable oil based adjuvants. Particularly preferred adjuvants include Agridex TM available from Helena Chemical, and X-77 (registered trademark) available from Valent U.S.A.

The compositions of this invention can also include extenders. In such a case, the compounds employed in the compositions of this invention can be extended with a carrier material (extender) of the kind used and commonly referred to in the art as inert solids, water and organic liquids.

The compounds employed in this invention will be included in sufficient amounts so as to provide the desired effect. Usually, the formulation will contain from about 0.5 to 95% by weight of such compounds. Obviously, higher amounts of compounds in the formulation will require that lesser amounts of the formulation be applied per acre to obtain the desired application rate of the compounds.

Solid compositions can be made with inert powders. The compositions thus can be homogeneous powders that can be used as such, diluted with inert solids to form dusts, or suspended in a suitable liquid medium for spray application. The powders usually comprise the active ingredients admixed with minor amounts of conditioning agent. Natural clays, either absorptive, such as attapulgite, or relatively non-absorptive, such as china clays, diatomaceous earth, synthetic fine silica, calcium silicate and other inert solid carriers of the kind conventionally employed in powdered herbicidal compositions can be used. The active ingredients usually make up from 0.5-90% or these powder compositions. The solids ordinarily should be very finely divided. For conversion of the powders to dusts, talc, pyrophyllite, and the like, are customarily used.

Liquid compositions including the active compounds described above can be prepared by admixing the compounds with a suitable liquid diluent medium. Typical of the liquid media commonly employed are methanol, benzene, toluene, and the like. The active ingredients usually make up about 0.5 to 50% of these liquid composition. Some of these compositions are designated to be used as such, and others to be extended with large quantities of water.

Compositions in the form of wettable powders or liquids can also include one or more surface-active agents, such as wetting, dispersing or emulsifying agents. The surface-active agents cause the compositions of wettable powders or liquids to disperse or emulsify easily in water to give aqueous sprays.

The surface-active agents employed can be of the anionic, cationic or nonionic type. They include, for example, sodium long-chain carboxylates, alkyl aryl sulfonates, sodium lauryl sulfate, polyethylene oxides, lignin sulfonates and other surface-active agents.

When used as a pre-emergent treatment, it is desirable to include a fertilizer, an insecticide, a fungicide or another herbicide.

While the compositions of the present invention are, in general, herbicidal in both pre- and post-emergent applications, the post-emergent application is preferred particularly in view of the acceleration of the post-emergent herbicidal activity against grassy weeds demonstrated by the compositions of this invention.

For pre-emergent control of undesirable vegetation, the herbicidal compositions will be applied in herbicidally effective amounts to the locus or growth medium of the vegetation, e.g., soil infested with seeds and/or seedlings of such vegetation. Such application will inhibit the growth of or kill the seeds, germinating seeds and seedlings.

For post-emergent applications, the herbicidal compositions of the invention will be applied directly to the foliage and other plant parts. Generally, the herbicidal compositions of the invention are especially effective against grassy weeds because of its accelerated activity against such weeds. The herbicidal composition of the invention is also especially effective in providing for a rapid burndown of both grassy weeds and dicotyledonous weeds as is required in no-till planting of crops. However, when so used, it is necessary that the herbicidal composition employ a herbicidally effective amount of 2-[7-fluoro-3,4-dihydro-3-oxo-4-(2-propynyl)-2H-1,4-benzoxazine-6-yl]-4,5,6,7-tetrahydro-1H-isoindole-1,3(2H)-dione. Also, when such a composition is used in no-till planting, it is preferable that the composition be applied either prior to planting of the crop seeds or after planting of such seeds but prior to emergence of the seedlings so as to avoid possible damage or injury to the crop. In general, the composition can be applied up to about 30 days prior to planting of the seeds, although preferably up to about 7 days prior to planting Likewise, after planting the seeds and unless already so applied, the composition is preferably applied at any time after planting and prior to the emergence of the seedlings.

In a preferred embodiment, the composition of the invention is applied shortly after, e.g., 1 to 3 days, planting of the seeds so as to substantially minimize the likelihood of seedling emergence.

However, if after crop emergence application of the composition of the invention is desired, such application should not be applied to the crop since contact with the crop can result in crop damage. Methods of applying herbicidal compositions without contacting emerged crops are known in the art, e.g., post-directed applications.

The following preparatory examples are directed to the preparation of the compounds employed in the present invention.

PREPARATORY EXAMPLE A

Preparation of 2-[1-(3-trans-chloroallyloxyimino) propyl]-5-(2-ethylthiopropyl)-3-hydroxy-b 2-cyclohexen-1-one In this example, 17.2 g (0.0636 mol) of 2-propionyl-5-(2-ethylthiopropyl)cyclohexane-1,3-dione; 0.9 g (0.0153 mol) of acetic acid, and 10 9 g (0.0757 mol) of 3-trans-chloroallyloxyamine in 35 ml of water are added to 20 ml of hexane and stirred. Aqueous 5 wt. percent sodium hydroxide is slowly added over about 15 minutes until 3.0 g (0.0757 mol+small excess) of sodium hydroxide is added—pH of reaction mixture about 6. The mixture is heated to and maintained at 40° C. for 2½ hours and then cooled to room temperature. The organic (i.e., hexane) phase is separated and washed with 10 ml of aqueous 5 weight percent hydrochloric acid and then aqueous 6.25 weight percent sodium hydroxide added until pH 12. The aqueous phase is separated and admixed with 25 ml of hexane and the pH adjusted to 5.4 by the dropwise addition of aqueous 36 weight percent hydrochloric acid over an ice bath. The organic phase is separated, dried over magnesium sulfate and then concentrated by evaporation affording the crude product. The crude product is purified by column chromatography over silica gel eluting with hexane:methylene chloride affording the purified title compound.

PREPARATORY EXAMPLE B

Preparation of 2-[7-fluoro-3,4-dihydro-3-oxo-4-(2-propynyl)-2H-1,4-benzoxazine-6-yl]-4,5,6,7-tetrahydro-1H-isoindole-1,3(2H)-dione A. Iron powder (36.42 g) is suspended in 5% aqueous acetic acid (69 ml) and heated to 80° C. To the suspension, a solution of ethyl 5-fluoro-2-nitrophenoxyacetate (15.86 g) in acetic acid (65 ml) and ethyl acetate (65 ml) is dropwise added, and the resulting mixture is heated at 60° to 80° C. under reflux for 3 hours. After removal of residue by filtration, the filtrate is extracted with ethyl acetate. The extract is washed with water and sodium bicarbonate solution, dried and concentrated to give 7-fluoro-3,4-dihydro-3-oxo-2H-1,4-benzoxazine.

B. A solution of 7-fluoro-3,4-dihydro-3-oxo-2H-1,4-benzoxazine (2.0 gram) in 80% aqueous sulfuric acid (30 ml) is cooled to 0° to 5° C., and 60% nitric acid (1.6 g) is gradually added thereto at 0° to 5° C. The resultant mixture is stirred at the same temperature for 30 minutes and poured onto ice water. The precipitated crystals are collected by filtration, washed with water and dried to give 7-fluoro-3,4-dihydro-3-oxo-6-nitro-2H-1,4-benzoxazine.

C. A suspension of sodium hydride (0.06 g) in N,N-dimethylformamide (3 ml) is cooled to 0° C. 7-fluoro-3,4-dihydro-3-oxo-6-nitro-2H-1,4-benzoxazine (0.57 g) is added thereto at between 0° to 5° C., and the resultant mixture is stirred for 30 minutes. Propargyl bromide (0.35 g) is added to the mixture, which is gradually heated to room temperature, and the reaction is continued for 6 hours. After addition of water, the resultant mixture is extracted with ethyl acetate, and the extract is washed with water, dried and concentrated. The residue is purified by silica gel thin layer chromatography using a 1:1 mixture of ethyl acetate and n-hexane as the eluent to give 7-fluoro-3,4-dihydro-3-oxo-6-nitro-4-(2-propynyl)-2H-1,4-benzoxazine.

D. Iron powder (1.05 g) is suspended in 5% aqueous acetic acid (2.0 ml) and heated to 80° C. To the suspension, a solution of 7-fluoro-3,4-dihydro-3-oxo-6-nitro-4-(2-propynyl)-2H-1,4-benzoxazine (0.47 g) in acetic acid (1.9 ml) and ethyl acetate (1.9 ml) is dropwise added, and the resulting mixture is heated under reflux at 60° to 80° C. for 3 hours. After being allowed to cool, water and ethyl acetate are added to the mixture. The residue is removed by filtration, and the filtrate is extracted with ethyl acetate. The extract is washed with water and aqueous sodium bicarbonate solution, dried and concentrated to give 6-amino-7-fluoro-3,4-dihydro-3-oxo-4-(2-propynyl)-2H-1,4-benzoxazine.

E. A mixture of 6-amino-7-fluoro-3,4-dihydro-3-oxo-4-(2-propynyl)-2H-1,4-benzoxazine (0.31 g), 3,4,5,6-tetrahydrophthalic anhydride (0.28 g) and acetic acid (3 ml) is heated under reflux for 2 hours. After being allowed to cool, water is added to the mixture, which is then extracted with ethyl acetate. The organic layer is washed with water, neutralized with sodium bicarbonate solution, dried and concentrated. The residue is purified by silica gel thin layer chromatography using a (1:2) mixture of ethyl acetate and hexane as the eluent to give the title product.

The following example is offered to illustrate the invention and should not be construed in any way as limiting the scope of this invention.

EXAMPLE 1

Post-Emergent Herbicidal Test

Test compositions were formulated by combining the requisite amount of the compound 2-[1-(3-trans-chloroallyloxyimino)propyl]-5-(2-ethylthiopropyl)-3-hydroxy-2-cyclohexen-1-one and the compound 2-[7-fluoro-3,4-dihydro-3-oxo-4-(2-propynyl)-2H-1,4-benzoxazine-6-yl]-4,5,6,7-tetrahydro-1H-isoindole-1,3(2H)-dione into an aqueous formulation so as to provide, when applied, the concentrations set forth in Table I. When applied, each of these formulations also contained Agridex ™ —available from Helena Chemical, at a concentration sufficient to provide 1 quart of Agridex ™ per treated acre.

TABLE I

| Formulation No. | Concentration of Compound[a] | | |
|---|---|---|---|
| | A | B | C |
| 1 | 10.120 g/acre | — | — |
| 2 | 20.240 g/acre | — | — |
| 3 | 30.360 g/acre | — | — |
| 4 | 10.120 g/acre | 0.1 lb/acre | — |
| 5 | 20.240 g/acre | 0.1 lb/acre | — |
| 6 | 30.360 g/acre | 0.1 lb/acre | — |
| 7 | — | 0.1 lb/acre | — |
| 8 | — | 0.1 lb/acre | 0.37 lb/acre |

[a]concentration of compound as applied.
A = 2-[7-fluoro-3,4-dihydro-3-oxo-4-(2-propynyl)-2H-1,4-benzoxazine-6-yl]-4,5,6,7-tetrahydro-1H-isoindole-1,3(2H)-dione
B = 2-[1-(3-trans-chloroallyloxyimino)propyl]-5-(2-ethylthiopropyl)-3-hydroxy-2-cyclohexen-1-one
C = Metribuzin - commercially available as Sencor available from Mobay Chemical Company and used herein as a post-emergent herbicide with activity against dicotyledonous weeds Each of these 8 test compositions were applied by foliar spray to the weeds under the following conditions: Row spacing 40 inches, gallons per acre 20, PSI 20, nozzle size 8003, number of nozzles 4, nozzle spacing 20 inches, applicator speed 3.16 miles per hour, air temperature 62° F., soil temperature 69° F., soil moisture-good, wind speed 0-3 miles per hour from the south, weed stages Rhizome johnsongrass (*sorghum halepense*) 2-24 inches; teaweed (*sida spinosa*) 2 inches, 6 leaves; cocklebur (*Xanthium Pensylvanicum*) 3 inches; and spurge (*euphorbia maculata*) 0.5 to 3 inches, 3 leaves. Of the above weeds, the first weed is a grassy weed whereas the remaining three weeds are dicotyledonous weeds. After application, the percent kill of each of the weeds was visually determined at 3, 7 and 21 days after treatment. The results are set forth in Tables II-V below.

TABLE II

| Formulation No. | Percent kill of Rhizome johnsongrass | | |
|---|---|---|---|
| | Days After Treatment | | |
| | 3 | 7 | 21 |
| 1 | 45.00 | 22.50 | 0 |
| 2 | 50.00 | 22.50 | 0 |
| 3 | 52.50 | 22.50 | 0 |
| 4 | 94.25 | 96.50 | 75.00 |
| 5 | 96.50 | 97.00 | 73.75 |
| 6 | 96.00 | 97.00 | 82.50 |
| 7 | 32.50 | 50.00 | 92.50 |
| 8 | 2.50 | 20.00 | 40.00 |

TABLE III

| Formulation No. | Percent kill of Teaweed | | |
|---|---|---|---|
| | Days After Treatment | | |
| | 3 | 7 | 21 |
| 1 | 95.25 | 91.00 | 83.75 |
| 2 | 98.75 | 97.25 | 89.75 |
| 3 | 97.75 | 97.75 | 96.25 |
| 4 | 97.50 | 94.75 | 86.25 |
| 5 | 98.75 | 98.00 | 94.25 |
| 6 | 99.00 | 99.75 | 98.25 |
| 7 | 2.50 | 0.00 | 0.00 |
| 8 | 32.50 | 67.50 | 90.75 |

TABLE IV

| Formulation No. | Percent kill of cocklebur | | |
|---|---|---|---|
| | Days After Treatment | | |
| | 3 | 7 | 21 |
| 1 | 100.35[a] | 100.00 | — |
| 2 | 99.89 | 100.00 | — |
| 3 | 96.65 | 100.00 | — |
| 4 | 99.00 | 100.00 | — |
| 5 | 100.36[a] | 100.00 | — |
| 6 | 99.00 | 100.00 | — |
| 7 | 2.50 | 0.00 | — |
| 8 | 37.50 | 100.00 | — |

[a]percents over 100% were obtained as a result of computer extrapolations

TABLE V

| Formulation No. | Percent kill of spurge | | |
|---|---|---|---|
| | Days After Treatment | | |
| | 3 | 7 | 21 |
| 1 | 99.00 | 100.00 | 99.50 |
| 2 | 99.00 | 100.00 | 99.75 |
| 3 | 99.00 | 100.00 | 100.00 |
| 4 | 99.00 | 100.00 | 97.00 |
| 5 | 98.75 | 100.00 | 100.00 |
| 6 | 99.00 | 100.00 | 100.00 |
| 7 | 2.50 | 0.00 | 0.00 |
| 8 | 40.00 | 40.00 | 12.50 |

From the above data, it is seen that the herbicidal compositions containing the compound 2-[7-fluoro-3,4-dihydro-3-oxo-4-(2-propynyl)-2H-1,4-benzoxazine-6-yl]-4,5,6,7-tetrahydro-1H-isoindole-1,3(2H)-dione as the only active herbicidal agent (formulations 1, 2 and 3) show some activity against Rhizome johnsongrass after 3 and 7 days but none after 21 days. On the other hand, this compound shows excellent activity against teaweed, cocklebur and spurge. This data substantiates the fact that this compound is an excellent post-emergent herbicide against dicotyledonous weeds while possessing poorer post-emergent herbicidal activity against grassy weeds.

Also from the above data, it is seen that the herbicidal composition containing the compound 2-[1-(3-trans-chloroallyloxyimino)propyl]-5-(2-ethylthiopropyl)-3-hydroxy-2-cyclohexen-1-one as the only active herbicidal agent (formulation 7) possesses excellent post-emergent herbicidal activity against Rhizome johnsongrass 21 days after application but possesses poorer activity against Rhizome johnsongrass 3 or 7 days after application. On the other hand, this compound possesses little or no post-emergent herbicidal activity against dicotyledonous weeds. This data substantiates the fact that the post-emergent herbicidal activity of this compound against grassy weeds manifests itself over an extended period of time.

Again from the above data, it is seen that the herbicidal compositions containing both the compound 2-[7-fluoro-3,4-dihydro-3-oxo-4-(2-propynyl)-2H-1,4-benzoxazine-6-yl]-4,5,6,7-tetrahydro-1H-isoindole-1,3(2H)-dione and the compound 2-[1-(3-trans-chloroallyloxyimino)propyl]-5-(2-ethylthiopropyl)-3-hydroxy-2-cyclohexen-1-one as the only active herbicidal agents (formulations 4, 5 and 6) possess the expected herbicidal activity against dicotyledonous weeds. However, these compositions show substantially accelerated herbicidal activity for Rhizome johnsongrass as compared to formulation 7. Because the activity against Rhizome johnsongrass at 3 and 7 days after treatment exceeds the additive result of each of these compounds used separately, this data substantiates the fact this combination synergistically interacts to accelerate the post-emergent herbicidal activity against grassy weeds.

Lastly, comparison of the results of formulation 8 against formulation 7 substantiate that the combination of the compound of formulation 7, a grassy weed herbicide, with Metribuzen ™, a commercially available post-emergent herbicide for dicotyledonous weeds, results in antagonism between these compounds—at least with regard to the results of this combination against grassy weeds. On the other hand, the compounds employed in the compositions of this invention are not antagonistic toward each other, but are in fact synergistic.

What is claimed is:

1. A herbicidal composition comprising
   (a) a biologically inert carrier;
   (b) a herbicidally effective amount of the compound 2-[1-(3-trans-chloroallyloxyimino)propyl]-5-(2-ethylthiopropyl)-3-hydroxy-2-cyclohexen-1-one or a herbicidally effective salt thereof; and
   (c) an effective amount of the compound 2-[7-fluoro-3,4-dihydro-3-oxo-4-(2-propynyl)-2H-1,4-benzoxazie-6-yl]-4,5,6,7-tetrahydro-1H-isoindole-1,3(2H)-dione to accelerate the herbicidal activity of the compound of (b) above with the proviso that said effective amount is not herbicidally effective.

2. The herbicidal composition according to claim 1 which additionally comprises a herbicidally effective adjuvant.

3. The herbicidal composition according to claim 2 wherein said herbicidally effective adjuvant is selected from the group consisting of a surfactant, a petroleum based oil, and a vegetable based oil.

4. The herbicidal composition according to claim 1 wherein the compound 2-[7-fluoro-3,4-dihydro-3-oxo-4-(2-propynyl)-2H-1,4-benzoxazine-6-yl]-4,5,6,7-tetrahydro-1H-isoindole-1,3(2H)-dione is employed at a rate of about 0.5 g/acre and greater.

5. A herbicidal composition comprising
   (a) a biologically inert carrier;
   (b) a herbicidally effective amount of the compound 2-[1-(3-trans-chloroallyloxyimino)propyl]-5-(2-ethylthiopropyl)-3-hydroxy-2-cyclohexen-1-one or a herbicidally effective salt thereof; and
   (c) a herbicidally effective amount of the compound 2-[7-fluoro-3,4-dihydro-3-oxo-4-(2-propynyl)-2H-1,4-benzoxazine-6-yl]-4,5,6,7-tetrahydro-1H-isoindole-1,3(2H)-dione.

6. The herbicidal composition according to claim 5 which additionally comprises a herbicidally effective adjuvant.

7. The herbicidal composition according to claim 6 wherein said herbicidally effective adjuvant is selected from the groups consisting of a surfactant, a petroleum based oil and a vegetable based oil.

8. The herbicidal composition according to claim 5 wherein the compound 2-[7-fluoro-3,4-dihydro-3-oxo-4-(2-propynyl)-2H-1,4-benzoxazine-6-yl]-4,5,6,7-tetrahydro-1H-isoindole-1,3(2H)-dione is employed at a rate of at least 10 g/acre.

9. A method for accelerating the herbicidal activity of the compound 2-[1-(3-trans-chloroallyloxyimino)propyl]-5-(2-ethylthiopropyl)-3-hydroxy-2-cyclohexen-1-one or a herbicidally effective salt thereof which comprises employing in combination with a herbicidally effective amount of said compound an effective amount of the compound 2-[7-fluoro-3,4-dihydro-3-oxo-4-(2-propynyl)-2H-1,4-benzoxazine-6-yl]-4,5,6,7-tetrahydro-1H-isoindole-1,3(2H)-dione to accelerate the herbicidal activity of said former compound with the proviso that said effective amount of the compound 2-[7-fluoro-3,4-dihydro-3-oxo-4-(2-propynyl)-2H-1,4-benzoxazine-6-yl]-4,5,6,7-tetrahydro-1H-isoindole-1,3(2H)-dione is not herbicidally effective.

10. The method according to claim 9 wherein said combination additionally contains a herbicidally effective adjuvant.

11. The method according to claim 10 wherein said herbicidally effective adjuvant is selected from the group consisting of a surfactant, a petroleum based oil, and a vegetable based oil.

12. The method according to claim 9 wherein said 2-[7-fluoro-3,4-dihydro-3-oxo-4-(2-propynyl)-2H-1,4-benzoxazine-6-yl]-4,5,6,7-tetrahydro-1H-isoindole-1,3(2H)-dione is employed at a rate of about 0.5 g/acre and greater.

13. A method for killing grassy weeds which comprises applying to said grassy weeds or their growth medium the composition according to claims 1, 2, 3 or 14. A method for killing grassy weeds and dicotyledonous weeds which comprises applying to said weeds or their growth medium a herbicidally effective amount of the composition according to claims 5, 6, 7 or 8.

15. A method for the no-till planting of crops which comprises applying to the area planted with seeds for said crops either before or after the planting of said seeds, a herbicidally effective amount of the composition according to claims 5, 6, 7 or 8.

16. The method according to claim 15 wherein said crops are selected from the group consisting of soybeans, corn, peanuts, cotton, rice, and grain sorghum.

17. A herbicidal composition according to claim 1 wherein said compounds defined in (b) and (c) are employed in a ratio of (b) to (c) of from about 2.5:1 to about 225:1.

18. A herbicidal composition according to claim 5 wherein said compounds defined in (b) and (c) are employed in a ratio of (b) to (c) of from about 1:1.5 to about 10:1.

* * * * *